(12) United States Patent
Ilia

(10) Patent No.: US 6,463,309 B1
(45) Date of Patent: Oct. 8, 2002

(54) APPARATUS AND METHOD FOR LOCATING VESSELS IN A LIVING BODY

(76) Inventor: Hanna Ilia, 1157 Morgan Rd., Lafayette, TN (US) 37083

( * ) Notice: Subject to any disclaimer, the term of this patent is extended or adjusted under 35 U.S.C. 154(b) by 0 days.

(21) Appl. No.: 09/568,722

(22) Filed: May 11, 2000

(51) Int. Cl.[7] ................................................. A61B 5/00
(52) U.S. Cl. ........................ 600/310; 600/407; 600/473; 600/476; 600/477; 600/479; 382/128; 382/130
(58) Field of Search ................................. 382/128, 130; 609/473, 476, 310, 407, 477

(56) References Cited

U.S. PATENT DOCUMENTS

| | | |
|---|---|---|
| 3,745,989 A | 7/1973 | Pinna |
| 3,782,365 A | 1/1974 | Pinna |
| 3,998,210 A | 12/1976 | Nosari |
| 4,527,569 A | 7/1985 | Kolb |
| 4,667,679 A | 5/1987 | Sahota |
| 4,817,622 A | 4/1989 | Pennypacker et al. |
| 5,022,399 A | 6/1991 | Kiegeleisen |
| 5,167,629 A | 12/1992 | Vertenstein et al. |
| 5,300,086 A | 4/1994 | Gory et al. |
| 5,305,759 A * | 4/1994 | Kaneko et al. ............. 128/665 |
| 5,309,915 A | 5/1994 | Ember |
| 5,519,208 A | 5/1996 | Esparza et al. |
| 5,608,210 A | 3/1997 | Esparza et al. |
| 5,647,850 A | 7/1997 | Allen |
| 5,678,555 A | 10/1997 | O'Connell |

* cited by examiner

*Primary Examiner*—Marvin M. Lateef
*Assistant Examiner*—Jeoyuh Lin
(74) *Attorney, Agent, or Firm*—Frank J. Bonini, Jr.; Harding, Earley, Follmer & Frailey

(57) ABSTRACT

A method and apparatus for facilitating the locating of vessels in a living body, the apparatus having an enclosure for surrounding a portion of the living body, a light source positioned to illuminate the body portion, a sight for viewing into the enclosure, and a secondary light source for illuminating the interior of the enclosure, the method comprising the steps of transilluminating a body portion with a light source.

28 Claims, 3 Drawing Sheets

APPARATUS AND METHOD FOR LOCATING VESSELS IN A LIVING BODY

BACKGROUND OF THE INVENTION

1. Field of the Invention

The present invention relates to the field of medicine, and specifically to an apparatus for locating and viewing subcutaneous vessels.

2. Brief Description of the Related Art

In the field of medicine, it is common to administer fluids, and to take samples of human blood, by accessing the veins and arteries of patients. The withdrawal of blood with needles and the insertion of catheters are two common procedures which require percutaneous access to veins and arteries of a person. Fluids, such as, for example drugs, proteins and other nutrients are routinely delivered to patients by medical personnel. While some medications can be delivered orally, or intramuscularly, with a syringe and needle, in many cases it is necessary to deliver fluids and drugs directly, intravenously, into the blood stream. To do this, trained medical personnel are required to locate an appropriate vessel, such as a vein or artery, into which the fluids or drugs can be administered.

In addition, blood samples are usually obtained through veins. The puncture of a vein with a needle is a preferred way to obtain a patient's blood sample. Also, catheterization of veins and arteries may take place through insertion of an apparatus into the vessel.

While locating and puncturing veins and arteries in adults is routinely done, it is often very difficult to locate veins of certain individuals, such as obese individuals, whose arteries are not as close to the skin surfaces as those of a person of normal weight. It is also difficult for medical personnel to locate and puncture veins and arteries of persons with very low blood pressure, and infants whose arteries are difficult to locate.

Human arteries and veins are approximately 2 to 8 millimeters in diameter. In infants, again the problems of locating and puncturing veins and arteries in order to carry out medical procedures can be very difficult or impossible at times. While physicians and other trained medical personnel sometimes have difficulty locating the veins and arteries of a healthy adult human, even more challenging, and sometimes impossible, to locate and puncture the veins and arteries of an infant. Infants, like adults, at times require surgery, administration of treatment, or other medical procedures which mandate the delivery of intravenous fluids into a vessel. Blood sampling also requires access to an infant's blood vessels. Locating the vein of an infant can be crucial, especially in emergency situations, where it is important to find the veins as rapidly as possible so that any necessary procedures can be carried out. There is a great risk imposed on the infant patient when there is a delay in providing the needed intravenous fluid or drugs. Delay in these cases can be fatal. For example, an infant who is unable to receive a crucial intravenous delivery may dehydrate; or, if a sufficient blood sample cannot be obtained from the infant within the appropriate time frame, it may be impossible to provide the appropriate treatment, or know how much of a medication to administer.

In other instances, certain diseases require the intermittent administration of intravenous fluids. For example the treatments of many diseases, such as, major infections, renal disease, and cancer, may include continuous or intermittent intravenous therapy.

The most commonly used method for insertion of intravenous delivery devices, such as a catheter, is by percutaneous needle puncture, directly into a vessel. Again, finding the vein or artery is critical to a catheter set up.

Presently, knowledge of an infant's anatomy is essential, and, moreover, is relied upon where the tiny infant veins are not visible. Although one may well know an infant's anatomy, the location of veins in an infant, while having a generally identifiable location, can vary slightly in each infant. As a result, repeated needle sticks may take place before a successful puncture of the vessel is achieved. This can lead to infections due to the instances of the repeated needle sticks and their tendency to introduce bacteria into the individual. This can occur, even where the medical personnel uses the proper procedures. Therefore, even a commanding knowledge of infant anatomy does not ensure that one will find the infant's vein on the first attempt, or even at all.

When the vein cannot be found, for example, when taking a blood sample, or when inserting an intravenous line, time for treatment administration can be compromised. In these situations, where live-saving treatment must be administered, or a blood sample obtained, it is sometimes necessary to insert a needle or catheter in the bone, such as the tibia. This is very painful to the patient, but, where life-saving treatment or access to the blood is necessary, the bone must be pierced.

In order to locate veins, it is a common practice to constrict veins in a desired area to more clearly delineate the veins. Apparatus such as straps and bands have been used for this purpose. U.S. Pat. No. 5,647,850 issued on Jul. 15, 1997 to William Allen discloses a "Method and Apparatus for Vein Location" which uses an inflatable bladder which is disposed about a patient's limb to constrict the blood flow.

While problems locating veins and arteries have been recognized, there have been some known attempts to improve the ability to locate veins within the body. U.S. Pat. No. 3,745,989 issued on Jul. 17, 1973 to Sanford Pinna discloses a "Device for Locating Veins in Living Bodies" which provides a spring-tensioned sensor rod and a marking rod mounted for axial reciprocation to respond to the sensing of a vein to mark its location on the skin. Similarly, U.S. Pat. No. 3,782,365 issues on Jan. 1, 1974 to Sanford Pinna discloses a "Detector for Locating Veins in Living Bodies."

U.S. Pat. No. 3,999,210 provides a "Method of Locating Vein" which employs a temperature sensitive film for aiding in the locating of veins in the arm. The 210 patent utilizes a liquid crystal material which is encapsulated in a film, and is sensitive to temperature to provide color variations corresponding to the location of the veins.

Other attempts to locate veins have included ultrasonic devices, such as the "Device for Guiding a Surgical Needle into a Blood Vessel" disclosed in U.S. Pat. No. 4,527,569, issued on Jul. 9, 1985 to Peter Kolb. U.S. Pat. No. 5,309,915 issued on May 10, 1994 to Charles Ember, discloses an "Apparatus for Locating Veins and Arteries" which utilizes ultrasonic signals to locate the vessel and produce an audible tone. A signal processing device utilizing a Doppler type of device is disclosed in U.S. Pat. No. 4,667,679 entitled "Apparatus and Method for Positioning and Puncturing an Artery and a Vein." The '679 device provides an intermittent visible light or sound alert when the blood vessel is detected.

Infrared imaging has been used to obtain an image which is recorded on a video monitor. An example is U.S. Pat. No. 4,817,622 entitled "Infrared Imager for Viewing Subcutaneous Location of Vascular Structures and Method of Use"

issued on Apr. 4, 1989 to Carl Pennypacker, et al. The '622 device provides a television camera and monitor for viewing an appendage. Similarly, U.S. Pat. No. 5,519,208 entitled "Infrared Aided Method and Apparatus for Venous Examination" issued on May 21, 1996 to Joel Esparza, et al. uses irradiation of the surface area of a patient to locate veins of the individual. U.S. Pat. No. 5,608,210 also entitled "Infrared Aided Method and Apparatus for Venous Examination" issued on Mar. 4, 1997 to Joel Esparza, et al. discloses a headpiece which is worn by medical personnel when inserting a hypodermic needle into a vein. U.S. Pat. No. 5,678,555 issued on Oct. 21, 1997 to Peter O'Connell for a "Method of Locating and Marking Veins" discloses an infrared imaging camera and a remote viewing screen to locate the veins of a patient.

Other attempts to locate veins have involved invasive procedures where locating devices themselves, although provided to reduce trauma which can result from repeated or failed needle sticks, can also cause trauma. In U.S. Pat. 5,167,629 issued on Dec. 1, 1992 to Mathieu Vertenstein, et al., a "Vein Locator" is disclosed which is sutured to subcutaneous tissues at a fixed location relative to the vein. The '629 device utilizes protuberances which can be felt by palpating the patient's skin to locate the vein.

When carrying out procedures such an venapuncture, direct viewing of the vessel is preferred. In a person with readily visible veins, the medical personnel can easily locate the vein and perform the necessary puncture. It is this primary preferred method which is utilized whenever possible. A need exists for a device which will enable the method of directly locating and sighting vessels to be carried out in instances where the vessels are not readily observable, such as those of an infant.

A need exists for a better way to carry out the puncture of veins and arteries of infants. Specifically, it is desirable to avoid the consecutive needle sticks, to provide a time-saving, effective way to administer fluids and medicines through an intravenous line, as well as to draw blood for sampling, immediately as needed.

SUMMARY OF THE INVENTION

An apparatus for locating vessels of a patient in order to carry out medical procedures is provided. The vessels to be located can be veins or arteries. The present invention has particular applicability with respect to infants, whose veins are difficult to locate due to their small size and their location beneath the skin and tissue. The apparatus has a first light source which is positioned below the limb or appendage containing the vessel to be punctured. For example, the arm of an individual, such as an infant, may contain veins which can be punctured with a needle to obtain a blood sample. The first light source is preferably a cold light source which is positionable over a range of locations to maximize the visibility of vessels. Preferably, a support is provided on which the appendage or limb of the patient is positioned. The light source illuminates the limb from below. The light source is provided to have an intensity which can shine through the limb. This transillumination of the limb facilitates the exposure of the vein positions. A frame can be provided to support the limb and the light source. Preferably, an enclosure surrounds the limb area from which the blood sample is to be taken. One or more openings in the device provide access to the enclosed area such as, for example, apertures which can permit the hands of medical personnel to be inserted into the enclosed space in order to carry out the puncture of a vein or artery. Portholes can be provided, or alternately, can be fitted with sleeved gloves if a more sealingly enclosed environment is desired. A sight is provided at the top of the cover so that medical personnel can directly view the appendage. The sight can be provided as an opening, or can have one or more lenses associated therewith for enlarging, enhancing, or correcting the viewing.

An opening is provided in the side of the device through which the patient's arm is inserted so that the desired appendage or area thereof is positioned within the device. Baffles can also surround the arm at the entrance to limit excess light spillage into the device. Furthermore, if necessary, an optional opening at the opposite end can be provided to permit an appendage to pass therethrough, if necessary. The openings can have removable covers.

A positionable, secondary light source can be provided to illuminate the surface of the appendage within the device.

It is a primary object of the present invention to provide a novel device for locating the blood vessels of a patient, and particularly those patients whose veins are difficult to find, such as an infant.

It is another object of the present invention to accomplish the above objects by transilluminating an appendage to facilitate locating a vein or artery.

It is another object of the present invention to provide an apparatus which can reduce trauma associated with needle punctures, and which can facilitate the speed with which a vessel can be located and punctured.

It is another object of the present invention to provide a portable device which can be carried in the field, and powered by an energy cell or rechargeable power supply.

BRIEF DESCRIPTION OF THE DRAWING FIGURES

DETAILED DESCRIPTION OF THE PREFERRED EMBODIMENTS

Figure 1:
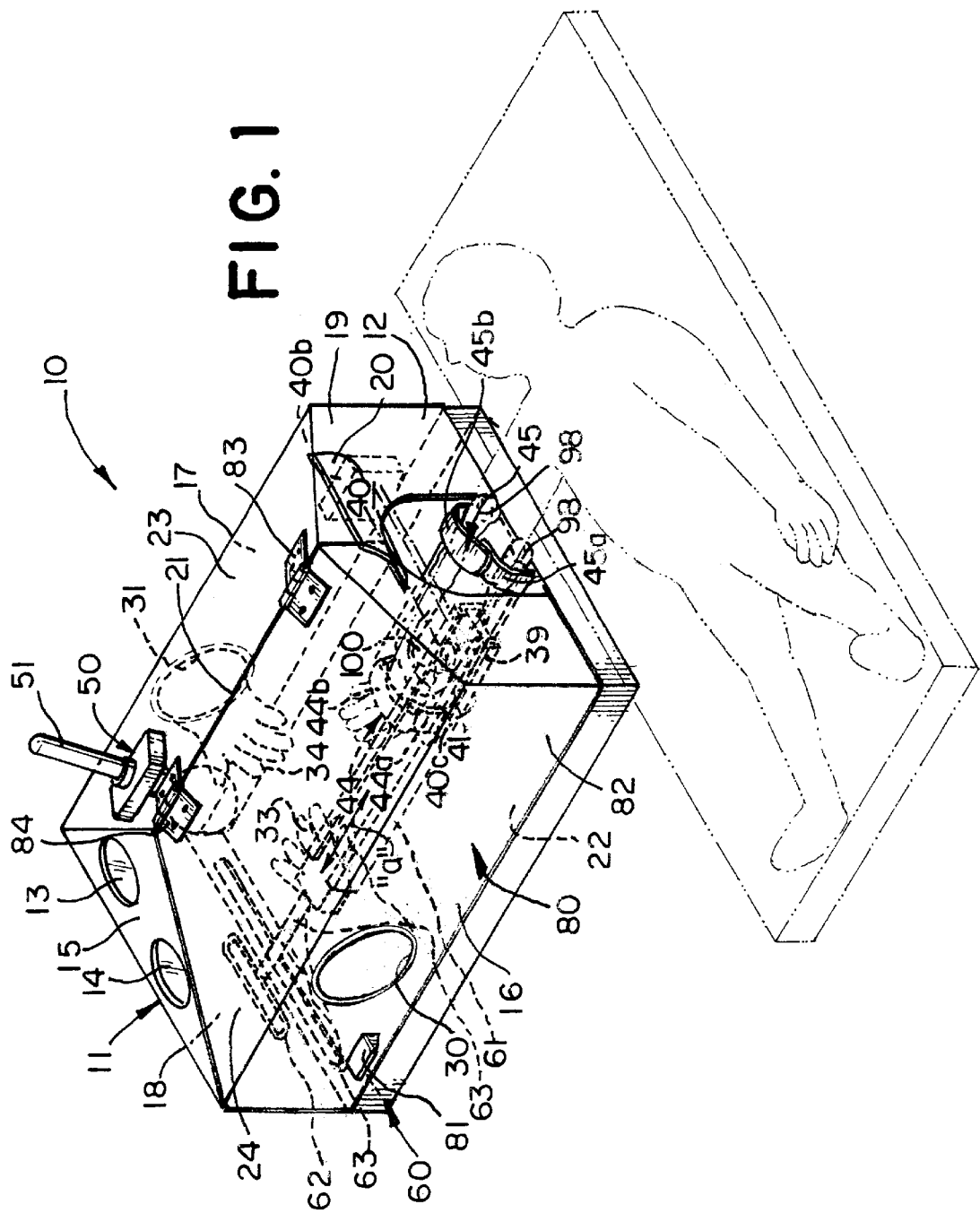
FIG. 1 is a perspective view of an apparatus for locating vessels in a living body.

Referring to FIG. 1, an apparatus 10 constructed in accordance with the present invention is shown comprising an enclosure 11 with an opening 12 therein for accommodating a body portion of a person, such as, for example, an arm 100 of an infant shown in broken-line representation. Sight means for viewing into the enclosure space is provided and is shown comprising a pair of apertures 13, 14 on a top wall portion 15 of the enclosure 11. The enclosure 11 has a first side wall 16, a second side wall 17, a front wall 18, a rear wall 19, a top wall 21 and a bottom wall 22. The top wall 21 can be formed from one or more wall portions, such as the first top wall portion 15, second top wall portion 23 and third top wall portion 24, with the first top wall portion 15 adjoining with an adjacent edge of the rear wall 19, and an adjacent edge of each of the second top wall portion 23 and third top wall portion 24, either directly or indirectly through a hinge or other connecting means.

Access means is provided for permitting access into the enclosure 11. Preferably, the access means can comprise apertures in the enclosure, such as the first and second apertures 30, 31 disposed in first and second side walls 16, 17, respectively. The apertures 30, 31 permit the medical personnel to insert his or her hands therethrough in order to carry out procedures in the enclosure 11, such as venapuncture, as discussed herein. The apertures 30, 31 can be provided sealed, with sealing means, such as the attached gloves 33, 34. The attached gloves 33, 34 can be removably provided to connect with and disconnect with the apparatus 10, as needed, and may be replaced as needed, in the event they are damaged, stained or contaminated.

Figure 2:
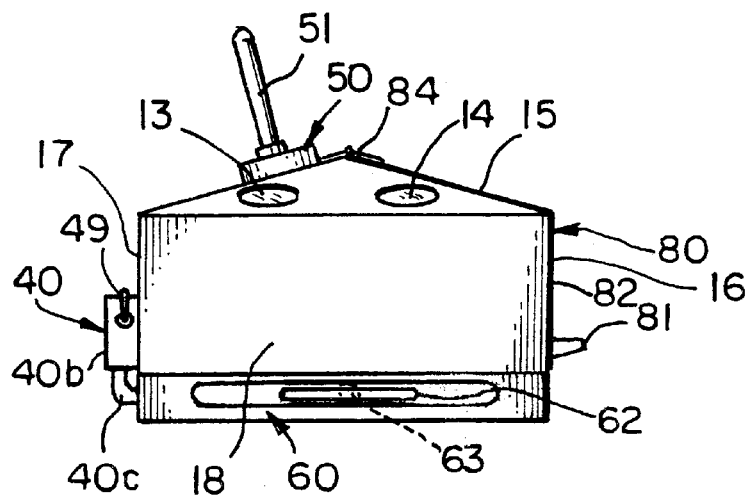
FIG. 2 is front elevation view of the apparatus of FIG. 1.
Figure 3:
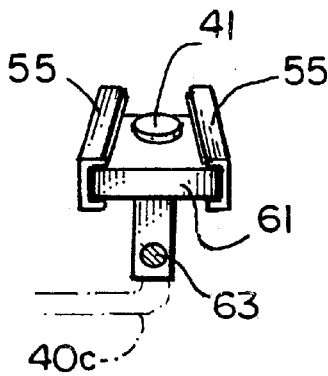
FIG. 3 is a front perspective separate view showing the moving means including a track along which the light can be moved.

Window means is provided on the bottom wall 22 for providing an opening to the enclosure 11. Light source means for supplying light, such as the light source 40 can be mounted below the bottom wall 22 or as shown in a preferred embodiment in FIGS. 1, 2 and 6, on a side wall 17 of the enclosure 11, to supply light to the body portion, such as the arm 100, when it is placed in the enclosure 11. The light source 40 can be switched with any conventional switching means, such as the switch 49 which comprises a commercially available switch, to permit the medical personnel using the device to turn on the light source 40 as needed. Preferably, moving means is provided to move the light 41 of the light source 40 over a range of positions. The light 41 of the light source 40 is movably provided, and as shown in FIG. 3, can be mounted on a slide means, such as the tracks 45 installed on the underside of the bottom wall 22, to provide a range of movement for the light 41 along the window means. The window means can comprise a window 39 disposed in the bottom wall 22. The window 39 can have support means on one or more of its edges for supporting the arm 100 of the body. The support means is shown comprising a foam material 42. The window 39 may be open or can have a clear cover which permits light to pass therethrough.

The apparatus 10 can also include holding means to hold the body portion 100 in place in the enclosure 11 to facilitate carrying out procedures, such as a venapuncture. The holding means can comprise a first strap 44 and a second strap 45. The straps 44, 45 can be provided in two sections, such as the first strap sections 44a, 45a, and second strap sections 44b, 45b, the sections 44a, 44b being selectively fastenable to each other to secure an arm 100 on the apparatus 10, and likewise, the sections 45a, 45b being selectively fastenable to each other. The first strap sections 44a, 45a can comprise on of a surface of hooks and loops, and the respective fastening second strap sections 44b, 45b can comprise the other of a surface of hooks and loops, such as that sold under the trademark VELCRO®. While two straps 44, 45 are shown, it is understood that more than two straps can be used for additional holding, or alternately, a single strap can be used.

The light source 40 preferably comprises a cold light source, and can be provided in the form of a fiber optic light 41 with a power source 40b and a tube 40c, which permits cold light to be directed to the body appendage 100. The light source 40 is provided having an intensity sufficient to permit the light to illuminate the body appendage 100. For example, the light source 40 can be powered by an external power supply, or any other suitable power source, such as a battery, or energy cell. The use of a rechargeable battery is particularly desirable for field applications, such as emergency medicine, where portability is desired and where electric outlets may not be available.

The light source means can comprise any suitable light which has sufficient intensity to illuminate the appendage, the arm 100. A battery-powered light, such as as incandescent bulb can be provided to comprise the light source. Other lights, such as, for example high intensity light sources which can be electrically or battery powered can be used. In one embodiment, according to the invention, the light source can comprise a low voltage light source, such as that commonly used with flashlight devices, which can be powered by battery cells, a power adapter, or other supply. In the event that a light is used which produces heat, it will be spaced a sufficient distance from the appendage, and limited in duration so that it is not allowed to remain on for an extensive period of time, in order to avoid potential damage to the limb 100 from excessive heat. The window 39, for example, can be fitted with a panel, such as, for example plexiglass, in order to help dissipate heat from the light source or insulate the appendage against the heat.

The transillumination of the arm 100 by the light from the light source means makes the veins of the arm visible when viewing the arm 100 from above, such as, for example with the light from the light source 40 being directed from below the arm 100. The light transmitted from the light source 40 illuminates the arm 100, and passes through the arm 100 and is visible to the medical personnel viewing it through the sight means. However, the veins do not permit the same amount of light to pass through as compared with those areas of the arm where there are no veins. The veins, therefore, become observable. Preferably, the light 41 is positioned to illuminate through the arm 100 by positioning the light 41 on the posterior side of the arm 100 and having it illuminate transversely through the arm 100 for viewing of vessels on the anterior side of the arm 100. When the light transmitted from the light source 40 is passed through the arm 100, locating the veins is facilitated so that a venapuncture can be carried out. To further facilitate carrying out procedures in the enclosure 11 of the apparatus 10, a second light source 50, which can be controlled by a switch 51 is provided to illuminate the working area in the enclosure 11. The second light source 50 can be switched on after the vein is located, so that once the vein is found a procedure can be carried out without having to relocate the patient, or the patent's arm 100. The switch 51 preferably is located near the sight means so that it can be operated with the head of the medical personnel using the device 10. Alternately, the switch 51 can be remotely located, such as by a foot switch, to enable the medical personnel to control the second light source 50, even when both hands are being used for other tasks. The switch 51 can also include dimmer circuitry, of the type known in the art and commercially available, for varying the intensity of the light output transmitted by the second light source 50. The second light source 50 can comprise any light-producing element, such as an incandescent light bulb, connected to a power supply, and for example can be run off of the same power supply 40b which powers the light 41 of the first light source 40.

Preferably, the enclosure 11 is provided to block out extraneous light so that light from the first light source 40 remains more concentrated to the observer, and the transillumination effect is more readily observed. The opening 12 in the rear wall 19 can have flaps 20 for sealing the enclosure 11 to further block outside light from spilling into the enclosure 11. A frame 60 is shown. The light source 40 is preferably supported on the frame 60 or on an enclosure wall.

Figure 4:
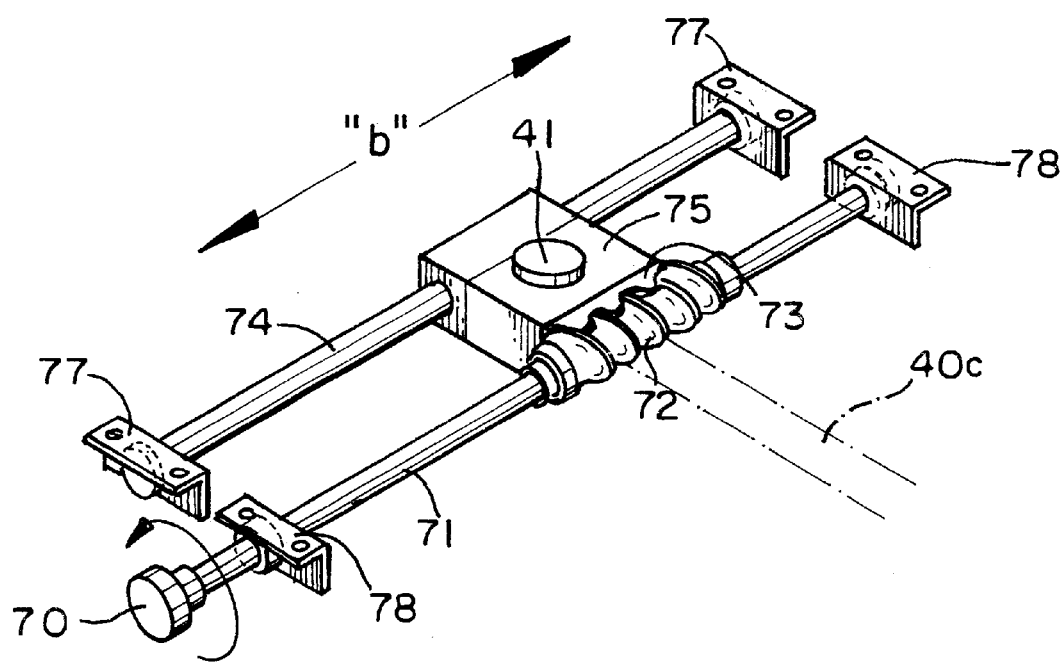
FIG. 4 is a front perspective separate view of an alternate embodiment of the moving means showing a gear arrangement.

The moving means for moving the position of the light 41 of the light source 40 can be supported on the frame 60 or bottom wall 22 of the enclosure 11. The moving means can comprise a slide member 61 connected to the light 41 to move the light 41 along the area of the window 39. The slide member 61 has a handle 62 connected by a rod 63 which can be operated to move the light 41 along the tracks 45 in the directions of arrow "a" to position the light 41. Alternately, the moving means can, for example, comprise a geared arrangement, where a knob can be used to turn a gear, such as a worm gear which can move the light source in either direction along double arrow "a". A geared moving means is shown in FIG. 4 comprising a knob 70, a shaft 71 connected to the knob 70 and having a first gear 72 thereon, and a second gear 73 disposed on the light 41 which meshes with the first gear 72, such that when the shaft 71 is rotated, the first gear 72 rotates with the shaft 71 and causes the light 41 to move along a slide rod 74 in either direction of arrow "b". The light 41 preferable is carried by a housing 75 which has a bore 76 through which the housing 75 is slidably mounted on the slide rod 74. The slide rod 74 preferably is supported on the apparatus 10 with mounting brackets 77. One or more mounting brackets 78 can secure the shaft 71 to the apparatus 10.

Figure 6:
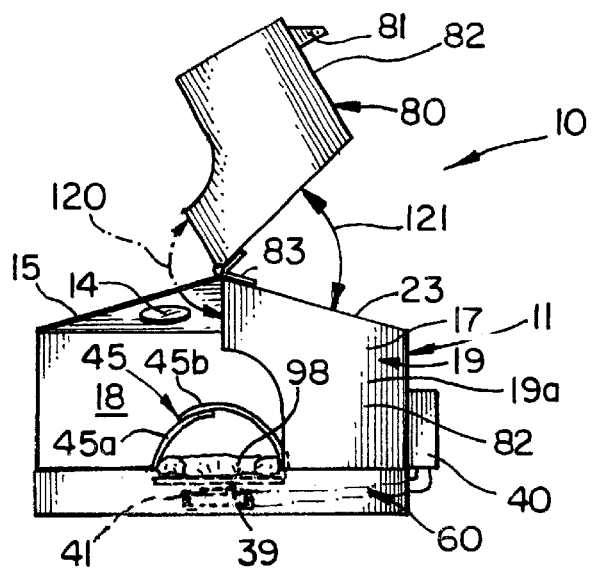
FIG. 6 is a rear elevation view of the apparatus of FIG. 1, shown with the cover partially lifted.

As shown best in FIGS. 1 and 6, a hinged cover 80 can also be provided to facilitate access to the enclosure 11. The cover 80 is formed by the third top wall portion 24, the first side wall 16 and a portion 19b of the front wall 19. The hinged cover 80 can further have a lifting handle 81, and can have gasketing means to assist in blocking extraneous light from entering into the enclosure 11. The gasketing means is shown comprising a gasket seal 82 which is disposed around the perimeter of the opening between the enclosure 11 and the hinged cover 80 so as to provide a gasket between the edges of the cover 80 and enclosure walls when the cover 80 is closed, as shown in FIG. 1. The gasket seal 82 can comprise a single element or a plurality of gasketing elements, and, for example can be formed from a rubber strip, or other suitable element. The hinged cover 80 is provided so that it can be lifted to rotate in the direction of double arrow 120 and further rotated to be positioned on the second top wall portion 23 of the enclosure 11 to rest thereon and remain in an open position after being rotated through the arc represented by double arrow 121. Similarly, the cover 80 can be closed by returning it from its open position to its closed (FIG. 1) position. Lifting is facilitated by the lifting handle 81. While a single lifting handle 81 is shown, it will be understood that a plurality of lifting handles can be provided, and the configuration of the lifting handle 81 shown comprising a lifting tab, can have alternate configurations which provide suitable ability to lift the cover 80. The lifting of the cover 80 preferably is done after a successful vein is located and needle stick has been performed. In this manner, the hand of the user which had previously extended through the first apperture 30 on the side wall 16 in order to carry out the procedure, is removed, while the other hand of the user extending through the second apperture 31 on the second side wall 17, can remain holding the needle in position on the patients appendage 100. This permits the right hand of the user to gain fall access and more mobility by reaching into the enclosure 11 once the cover 80 has been opened, as shown in FIG. 6. The cover 80 can be secured with the hinges 83, 84 which can attach to the cover surface formed by the third top wall portion 24 and enclosure second top wall portion 23. In addition, the interior surfaces of the first side wall 16, second side wall 17, front wall 19, rear wall 18, top wall 21 and bottom wall 22 can be coated or darkened so as to reduce the amount of light which may be reflected from the walls when locating a vessel.

Shade means can also be provided to cover the access means or first and second apertures 30, 31, in order to block extraneous light from entering the enclosure 11. The shade means can comprise a plurality of flaps or baffles 20 which are deflectable when the enclosure 11 is accessed, and which return to a position to block the aperture 30, 31 when an individual's hands are withdrawn from the enclosure 11.

Figure 5:
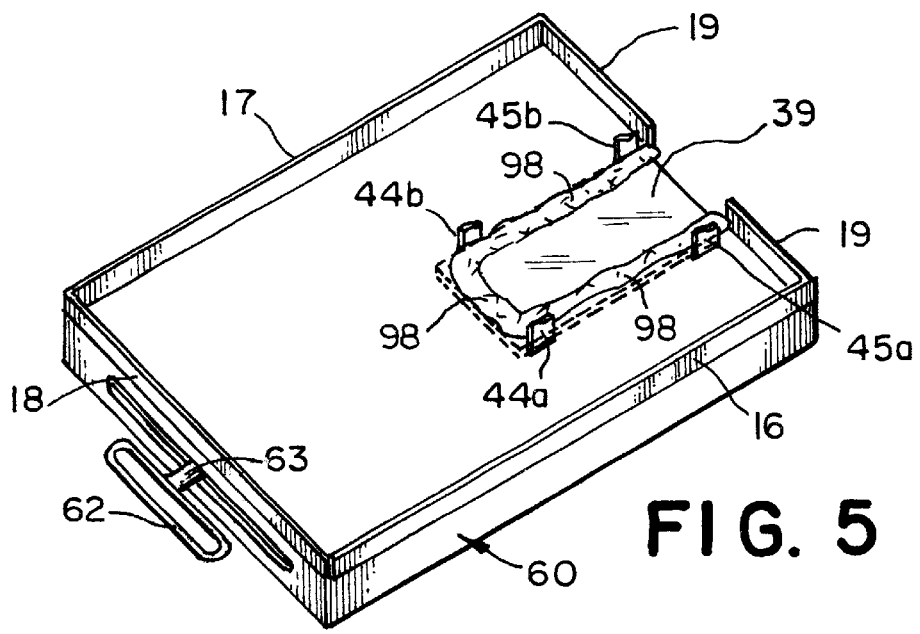
FIG. 5 is a top perspective sectional view taken through the enclosure.

As shown in FIG. 5, support means comprising a supporting material such as a foam or cushion 98 can be disposed around the window 39 to cushion the arm 100.

Figure 7:
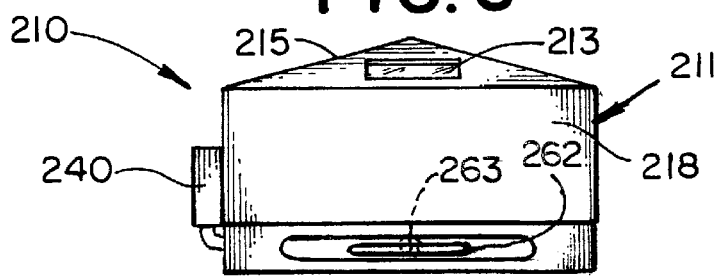
FIG. 7 is a front elevation view of an alternate embodiment of an apparatus according to the invention.

While the sight means is shown comprising apertures 13, 14 for viewing into the enclosure 11, it will be understood that one or more optical lenses can be provided to enhance the viewing of the body portion 100 and any medical instruments, such as needles or catheters used to carry out a venapuncture. For example, the sight means can further include corrective, and or magnifying lenses, including variable zoom lenses, such as those commercially available, for enhancing the viewing of the instruments and body portion in the enclosure 11. In an alternate embodiment shown in FIG. 7, the light means comprises a window 213 disposed in a top wall 215 of the enclosure 211. The device 210 is constructed similar to the invention described above in connection with FIGS. 1–6, and has a light source 240, means for moving the light, such as, for example the handle 262 and shaft 263. The remainder of the device 210 is not shown, however it will be understood to be constructed in the same manner as that described above and shown in FIGS. 1–6.

These and other advantages of the present invention will be understood from a reading of the background of the invention, the summary of the invention, the brief description of the drawing FIGS., the detailed description of the preferred embodiments, and the appended claims.

What is claimed is:

1. An apparatus for locating blood vessels in a portion of a living body comprising:
   a) a light source positioned adjacent a portion of a living body to illuminate the portion by directing light through said portion;
   b) an enclosure which is adapted to surround a portion of a body and has an opening therein; and
   c) sight means provided on said enclosure for viewing into the enclosure.

2. The apparatus of claim 1, wherein said light source is a cold light source which is a movably positionable over a range of positions.

3. The apparatus of claim 1, further comprising moving means for moving said light source.

4. The apparatus of claim 3, wherein said moving means comprises a track on which said light source is mounted for sliding movement.

5. The apparatus of claim 3, wherein said moving means comprises a knob connected to a shaft, a first gear mounted on said shaft for rotation therewith, and wherein said light source includes a gear in mesh with the first gear.

6. The apparatus of claim 1, wherein said sight means comprises a lens.

7. The apparatus of claim 1, further comprising a second light source for illuminating the enclosure.

8. The apparatus of claim 7, further comprising a switch connected with said second light source, wherein said second light source is switchable between on and off positions.

9. The apparatus of claim 7, further comprising means for varying the intensity of said second light source.

10. The apparatus of claim 1, wherein said enclosure has access means for permitting access through the enclosure.

11. The apparatus of claim 10, wherein said enclosure has at least a first side wall and a second side wall, and wherein said access means comprises a pair of apertures, each aperture being disclosed on a side wall.

12. The apparatus of claim 11, wherein said access means further includes sleeves with attached gloves connected to said apertures.

13. The apparatus of claim 10, further comprising shade means for blocking light, said shade means being disposed proximate to said access means and to removably cover said access means.

14. The apparatus of claim 1, wherein said light source has an intensity sufficient to illuminate a body portion of a living person.

15. The apparatus of claim 1, wherein said light source comprises a fiber optic light.

16. The apparatus of claim 1, wherein said sight means comprises a window provided on said enclosure adapted to permit viewing of a portion of a body placed in said enclosure.

17. The apparatus of claim 1, wherein said sight means comprises a lens having enlarging capabilities.

18. The apparatus of claim 1, wherein said sight means has a vision correcting lens provided with varying optical correction over a range.

19. The apparatus of claim 1 further comprising a liftable cover which is moveable from a closed position to an open position whereby the cover permits access into to the enclosure.

20. The apparatus of claim 1, wherein said enclosure has a bottom wall with a window therein.

21. The apparatus of claim 20 further comprises support means disposed adjacent the window for supporting a living body portion.

22. An apparatus for locating a vessel such as a vein or artery of an infant in order to facilitate the carrying out of a puncture of the vessel, the apparatus comprising:

a) an enclosure having support means adapted to support a body portion of an infant and at least one opening which is adapted to permit the insertion of a body portion of an infant therein;

b) a cold light source supported on said enclosure and being movably positionable, said cold light source being disposed below said body portion and directed to illuminate the body portion;

c) sight means provided on said enclosure for viewing into the enclosure;

d) wherein the light source is positioned on one side of an infant's body portion and wherein the vessel to be punctured is accessed on the opposite side of the infant's body portion;

e) closable apertures provided on said enclosure adapted for permitting insertion of the hands of a medical personnel into the enclosure.

23. The apparatus of claim 22, further comprising a second light source which is disposed within said enclosure to selectively illuminate the enclosure, and a switch to control the second light source.

24. The apparatus of claim 23, wherein said switch comprises a foot pedal.

25. The apparatus of claim 23, wherein said switch is disposed proximate to said light means and is adapted to be operated with a user's forehead.

26. The apparatus of claim 22, wherein said switch is provided at a location remote of the location of the light source.

27. A method for locating a vessel such as a vein or artery in a body portion of an infant, the method comprising the steps of:

a) providing a cold light source and positioning the cold light source below an infant's body portion;

b) surrounding an infant's body portion with a cover which substantially blocks light other than that emitted from the cold light source;

c) wherein the light source is movable and wherein the step of positioning the light source includes moving the light source.

28. A method for locating a vessel such as a vein or artery in a body portion of an infant, the method comprising the steps of:

a) providing an enclosure with at least one opening therein;

b) inserting an infant's body portion through said opening and into said enclosure;

c) providing a cold light source and positioning said cold light source below the infant's body portion;

d) illuminating the infant's body portion with the cold light source;

e) viewing the surface of the infant's body portion from the side opposite that which the light source is illuminating.

* * * * *